United States Patent [19]

Bubani

[11] Patent Number: Plant 6,380

[45] Date of Patent: Nov. 8, 1988

[54] PLUM TREE, "SHARRON'S"

[75] Inventor: Giovanni B. Bubani, Fresno, Calif.

[73] Assignees: R.E.U.S., Inc.; Pruner A.G.I.; Pruner A.G.II; Agri-Cal, Inc., all of Fresno, Calif.

[21] Appl. No.: 942,081

[22] Filed: Dec. 15, 1986

[51] Int. Cl.[4] ..... A01H 5/03

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of plum tree which is characterized by a date of maturity of July 26, under the cultural conditions prevailing at Sanger, Calif., which is approximately four days prior to the Casselman Plum Tree (U.S. Plant Pat. No. 1,756), with which it is most closely similar, and which is further distinguished as to novelty by producing a plum which has exceptional storage and shipping characteristics.

1 Drawing Sheet

BACKGROUND OF THE NEW VARIETY

The present invention relates to a new and distinct variety of plum tree which has been denominated varietally as the "Sharron's"; and more particularly to such a plum tree which produces relatively large fruit having red skin, which fruit ripens approximately four days before the fruit of the Casselman Plum Tree (unpatented), with which it most closely resembles when grown under the same or similar ecological conditions, and which is further distinguished from the Casselman Plum Tree by bearing fruit which are resistant to stem and shoulder end cracks, and whose flesh is resistant to heat damage.

As an agent of the Bacomar Corporation, a corporation organized and existing under the laws of the State of California; the inventor is from time to time employed for the purpose of locating or otherwise deriving or developing new varieties of fruit which may appear as chance seedlings or mutations in the various orchards of his employer's clients. In these labors, the applicant, in August of 1980, discovered a scaffold mutation within the cultivated area of an orchard which contained a mixed planting of Grand Rosa Plum Trees (U.S. Plant Pat. No. 1,756) and Black Knight Plum Trees (unpatented) which is owned by R.E.U.S. Inc; located at Riverbend and MacDonough Roads in Sanger, Calif. in the County of Fresno.

As should be understood, the relative dates of ripening of various varieties of plums are of extreme importance. It has long been recognized as desirable to provide a plum tree that bears fruit later in the season than other varieties of plum trees which it most nearly resembles whereby the fruit can be sent to market at a time when competition is at a minimum. In addition, if the harvesting periods of various plums can be effectively spread over a longer period of time, considerable savings and increased efficiency can be attained because the capital expenditures required to harvest and transport such fruit can be efficiently spread over a longer period of time resulting in lower cost of the final product, and increasing the uniformity of production.

ORIGIN AND ASEXUAL REPRODUCTION OF THE NEW VARIETY

The new and distinct variety of plum tree hereof was a scaffold mutation of a Grand Rosa Plum Tree (U.S. Plant Pat. No. 1,756), discovered in August, 1980 in a mixed planting of Grand Rosa Plum Trees; and Black Knight Plum Trees (unpatented) which are located on the ranch owned by R.E.U.S. Inc. which is located at the corner of Riverbend and MacDonough Roads in Sanger, Calif. The superior characteristics of the subject variety were observed, recognized and appreciated by the applicant at that time. The scaffold mutation was thereafter marked for future observation, and for asexual reproduction.

The applicant asexually reproduced the subject plum tree by removing bud wood from the scaffold mutation, in the winter of 1980, and thereafter grafting it onto test seedlings, in the early spring of 1981, which were located on the R.E.U.S. Ranch. The test seedlings of the present variety have been constantly observed by the applicant since discovery in 1980 and it has been determined that this first asexual propagation resulted in progeny being produced that were found to possess the same distinctive characteristics as the original seedling.

Inasmuch as the present variety was a scaffold mutation, its origin is unknown, although it was known by the applicant in the sense that he discovered it and thereafter asexually reproduced the mutation and tested the subject mutation at the designated Ranch of the R.E.U.S. Corporation at Sanger, Calif.

BRIEF DESCRIPTION OF THE DRAWING

The accompanying drawing is a color photograph of a characteristic twig bearing typical leaves, which displays the dorsal and ventral coloration thereof, two plums showing their external coloration sufficiently matured for harvesting and shipment, a plum halved transversely of the suture plane to illustrate the flesh coloration, and two stones all of the subject variety.

DETAILED DESCRIPTION

Referring more specifically to the pomological details of this new and distinct variety of plum tree, the following has been observed under the ecological conditions prevailing at the Ranch of R.E.U.S. Inc. of Sanger, Calif. All major color code designations are by reference to the "Dictionary of Color" by Maerz and Paul published in 1950. Common color names are also used occasionally in instances in which it is believed to be helpful to the description and simplification thereof.

TREE

Size: Above average.

Vigor: Above average.

Figure: Upright; vase formed, or spreading depending upon pruning practices.

Productivity: Productive; the new variety is hardy under typical San Joaquin Valley climatic conditions.

Regularity of bearing: Regular.

Trunk:

*Diameter.*—Variable, average to above average.

*Texture.*—Medium surface texture.

*Color.*—Older bark — variable, chestnut-brown, (15-H-17), to grayish-brown (7-C-8).

*Lenticels.*—Average in size and number.

Branches:

*Size.*—Mature one year old branches appear average in size.

*Surface texture — Mature branches.*—average, with moderate amounts of scarfskin.

*Surface texture — Immature shoots.*—smooth.

*Color — mature branches.*—Grayish-brown, (7-C-9).

*Color — immature shoots.*—Light green, (20-J-5).

*Lenticels.*—Mature branches and immature shoots — numerous.

LEAVES

Generally: All leaf measurements were procured from mature leaves that were growing at approximately the midpoint of an actively growing upright shoot of a current season's growth.

Size:

*Generally.*—Large.

*Average length.*—Approximately 14.8 cm.

*Average width.*—Approximately 6.0 cm.

Form:

*Generally.*—Broadly lanceolate.

*Leaf apex.*—Acuminate.

*Marginal form.*—Coarsely crenate, occasionally doubly so at the midpoint of the leaf margin; crenations appear deep and somewhat irregular; leaf margin appears very slightly undulate.

Color:

*Dorsal surface.*—Dark green, (24-H-8).

*Ventral surface.*—A light grayish-green, (21-E-6).

*Color — mid-vein.*—The color of the mid-vein on the ventral surface of the leaf is a light grey-green, (20-D-30); the width of this lightly colored mid-vein area is approximately one (1) millimeter, at its midpoint.

Leaf petiole:

*Generally.*—Moderately long.

*Length.*—Approximately 14 mm. to 16 mm.

*Thickness.*—Approximately 1.5 mm.

*Color.*—A light grayish-green, (20-D-3); however the petiole color can appear somewhat darker along the upper petiole groove.

Leaf glands:

*Size.*—Generally — medium.

*Form.*—Variable, reniform or occasionally globose.

*Arrangement.*—The glands of the subject variety appear occasionally stalked, although they are generally positioned on the petiole in an alternative pattern at a position just slightly below the basal leaf margin.

*Color.*—Light green (20-J-4).

*Texture.*—The leaf glands appear shiny and darken with age.

Stipules:

*Numbers.*—Variable; one or two stipules appear at the base of the leaf petiole.

*Size.*—Generally — medium to large.

*Length.*—Approximately 8 to 10 mm.

*Color.*—Light green, (20-F-4).

*Arrangement.*—The stipules are usually persistent.

Flower buds and flowers: The flower buds and flowers generally of the subject variety are not distinctive.

*Chilling requirements.*—Generally — during the 1986 and 1987 season the chilling requirement was calculated as approximately 1,000–1,100 hours at temperatures below 45 degrees Fahrenheit.

*Blooming time.*—Generally — blooming time is approximately mid-season with respect to other common plum varieties.

*Date of bloom.*—Full bloom — full bloom is achieved approximately March 3rd in the San Joaquin Valley, of Central California.

*Flower size.*—Generally — large.

*Flower size.*—Diameter — approximately 20 to 22 mm; however, some of the flowers of the subject variety remain slightly cupped even when fully mature.

*Bloom amount.—Generally — abundant as compared with other varieties.*

*Number of flower buds.*—Variable, often 4 to 6 flower buds can be detected on each node.

*Color.*—Flower Bud Scales — a light chestnut, (15-H-10).

*Size.*—Flower buds — medium.

*Form.*—Flower buds — conic.

*Flower petals.*—Size — large.

*Petal length.*—Approximately 11 to 12 mm.

*Petal width.*—Approximately 9 to 10 mm.

*Petal form.*—Generally — slightly obovate although occasionally oval ones may be detected.

*Claw.*—Short; The petals of the subject variety display moderate cupping inwardly.

*Petals.*—Color — White (9-A-1). Marginal form — variable, slightly to moderately undulate.

*Pedicels.*—Length — medium, approximately 8 to 9 mm. Thickness — approximately 1 mm. Color — Light green, (18-J-4).

Nectaries.—Color — young plants — Brown, (13-F-10). Color — mature plants — Brownish-green (12-K-7).

*Anthers.*—Color — Light yellow, (10-L-3). Size — medium.

*Pollen.*—Quantity — abundant. Color — Yellow, (10-L-3).

*Stamens.*—Length — approximately 7 to 9 mm; the stamens appear somewhat longer than the pistil when fully extended. Color — White, (9-A-1).

*Pistil.*—Length — approximately 8 mm. Color — Light green, (7-G-3).

FRUIT

Maturity for harvest: Variable; in 1986 the subject variety matured relatively early, that is on approximately July 26 at Sanger, Calif.; however in previous years the variety has matured on dates as late as August 18. The subject variety displays the desirable characteristic of hanging well on the trees thus permitting multiple picking over a period of approximately 10 days after the first picking.

Size:

*Generally.*—Large.

*Diameter in the cheek plane.*—Approximately 58 mm. to 61 mm.

*Diameter in the suture plane.*—Approximately 56 mm. to 62 mm.

*Diameter in the axial plane.*—Approximately 55 mm. to 58 mm.

Form:

*Uniformity.*—Uniform.

*Symmetry.*—Symmetrical; globose in the apical aspect, and broadly ovate in the lateral aspect.

Ventral surfaces:

*Shape.*—Variable, rounded; occasionally smooth to slightly lipped throughout; the variety has low shoulders and is generally more strongly lipped in the area near the basal end of the fruit.

Stem cavity:

*Shape.*—Moderately broad; oval in the suture plane. The variety has rounded shoulders.

*Length.*—Approximately 22 mm. to 24 mm.

*Width.*—Approximately 18 mm. to 20 mm.

*Depth.*—Generally — moderately deep, approximately 11 mm. to 13 mm.

*Texture.*—Some skin checking is evident in a pattern which is substantially circular around the inside surface of the stem cavity.

Base:

*Form.*—Rounded, and slightly truncate. The base most often appears at a right angle to the fruit axis, although it may occasionally be slightly oblique.

Apex:

*Form.*—Short and truncate.

*Position.*—The pistil point is apical and appears substantially flattened and depressed.

*Texture.*—Some calloused areas are present at the pistil point.

Suture:

*Generally.*—The suture is a narrow depression which extends from the base to the apex; the apex is usually quite prominent, although width, coloration and depth may vary from fruit to fruit.

*Color.*—Variable, although usually a dark garnet red, (6-L-6).

*Form.*—The suture deepens and narrows over the basal shoulder; the suture in the area of the basal shoulder appears somewhat lighter in color than the remainder of the suture.

*Width.*—Variable, the suture is usually widest approximately at mid-suture toward the apex; approximately 1 mm. to 2 mm. in width.

Stem:

*Generally.*—Medium to short.

*Length.*—Approximately 10 mm. to 12 mm.

*Thickness.*—Approximately 1.5 mm.

*Color.*—Variable; olive green, (13-J-4), to light brown, (13-I-8).

Skin:

*Thickness.*—Generally — medium to slightly above average.

*Tenacious to flesh.*—Yes.

*Texture.*—Mediumly coarse; slightly acidic in flavor.

*Tendency to crack.*—Not observed.

*Bloom.*—A heavy grey bloom is typically present over the entire skin surface.

*Pubescence.*—Not evident.

*Color.*—Variable; approximately 80% to 95% of the skin color appears as a bright cherry red (5-L-10), to a deep garnet red (7-L-6) with some gradations therebetween.

*Ground color.*—Yellow-chamois, (11-K-6); this color appears most commonly over approximately 5% to 20% of the surface area of the fruit; the surface area affected is located in the basal shoulder areas where the fruit has been shaded by leaves or branches.

*Blush color.*—Generally — the blush color does not appear in any particular uniform pattern. The color intensity of the blush varies over the entire surface of any individual fruit.

*Dots.*—Numerous; the dots and other speckling appear over the entire surface of the fruit, although the dots appear more concentrated over the apical shoulders and around the apex.

Flesh:

*Surface texture.*—Firm, slightly coarse, and juicy.

*Fibers.*—Present; average in length and in numbers; fine and tender.

*Ripening.*—Even.

*Flavor.*—Sweet, mildly acidic, pleasant.

*Aroma.*—Slight.

*Flesh color.*—Generally — a uniform yellow throughout, (10-H-6); a slightly darker flesh color may appear in the stone cavity.

*Eating quality.*—Above average.

*Aroma.*—Slight.

Stone:

*Freestone or clingstone.*—Semi-freestone. The stone of the subject variety will readily break free along the dorsal suture but will cling somewhat to the flesh along the ventral surface and to the basal shoulders.

*Size.*—Generally — medium.

*Length.*—Approximately 20 mm. to 23 mm.

*Width.*—Approximately 18 mm. to 20 mm.

*Thickness.*—Approximately 10 mm. to 12 mm.

*Fibers.*—Present; average in length and in numbers.

*Form.*—Generally ovate, with a prominent ventral suture edge.

*Base.*—Generally rounded, the stone displays an unusually eroded hilum area; the base is disposed at right angles to the stone axis.

*Hilum.*—Generally — large, and narrowly oval.

*Form.*—Heavily eroded with the basal shoulder of the ventral suture overlying the cavity formed by the hilum erosion.

*Apex.*—Rounded; the tip is very short, low and inconspicuous.

*Sides.*—Form — nearly equal and symmetrical.

*Texture.*—Generally — slightly rippled but free from pitting and without the presence of the strong ridges.

*Grooves.*—Most commonly one deep groove appears on each side of the stone and extends roughly parallel to the ventral suture and converges apically and basally.

*Ventral edge.*—Generally — thick and moderately prominent. The ventral edge appears jagged at the basal end and overlies the eroded hilum scar.

*Dorsal edge.*—Generally — a deep and moderately wide groove extends along one-third of the dorsal edge from the base to a position somewhat below mid-suture. Several deep pits appear at approximately the middle third of the suture edge with the suture groove almost not visible at this point. A tight narrow groove appears over the apical shoulder and extends to the apex; this narrow groove appears moderately eroded at times.

*Stone color.*—Dry — the stone color is variable, buff to light brown (11-H-7).

*Tendency to split.*—Not evident.

Use of plum: Fresh market; for both local and long distance markets.

Keeping quality: Exceptional; the subject variety has been kept in cold storage for extended periods of time with no deleterious effects noted.

Shipping quality: Noteworthy.

Resistance to diseases and insects: The Sharron's Plum Tree shows an improved resistance to brown rot, fungal infections; no other susceptibilities known.

Although the new variety of plum tree possesses the described characteristics when grown under the growing conditions prevailing in Sanger, Calif., in the central part of the San Joaquin Valley, it is to be understood that variations of the usual magnitude and characteristics incident to growing conditions, fertilization, pruning and pest control are to be expected.

Having thus described my new variety of Plum Tree, what is new and desired to be secured by Letters Patent is:

1. A new and distinct variety of Plum Tree substantially as illustrated and described which is somewhat similar to the Casselman Plum Tree, (U.S. Plant Pat. No. 1,756), with which it most closely resembles, but from which it is distinguished therefrom by bearing fruit which are larger, uniform and a full dark red color, which ripens approximately July 26 to August 18 at Sanger, Calif., and which further has a firm yellow colored flesh which resists heat damage and a skin which shows a resistance to shoulder and stem end cracks; the variety displaying exceptional handling and shipping characteristics.

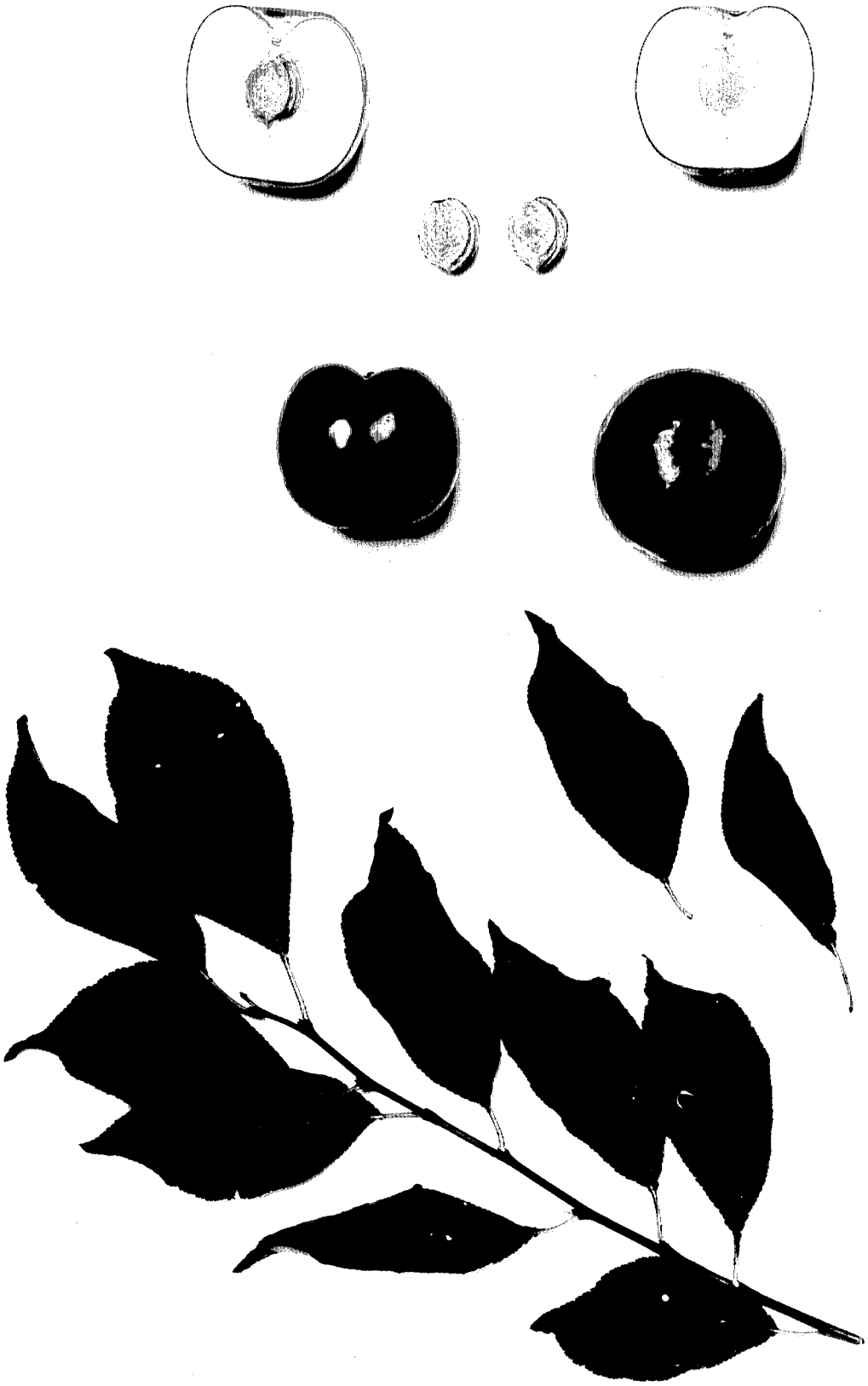

* * * * *